(12) United States Patent
Aloise et al.

(10) Patent No.: US 7,779,542 B2
(45) Date of Patent: Aug. 24, 2010

(54) METHOD OF MANUFACTURING A DENTAL INSTRUMENT

(75) Inventors: Carlos A. Aloise, Chino, CA (US); Gary T. Garman, La Verne, CA (US)

(73) Assignee: Ormco Corporation, Orange, CA (US)

( * ) Notice: Subject to any disclaimer, the term of this patent is extended or adjusted under 35 U.S.C. 154(b) by 1303 days.

(21) Appl. No.: 11/216,890

(22) Filed: Aug. 31, 2005

(65) Prior Publication Data

US 2006/0014480 A1 Jan. 19, 2006

Related U.S. Application Data

(60) Continuation-in-part of application No. 10/797,552, filed on Mar. 10, 2004, now Pat. No. 7,207,111, which is a division of application No. 10/125,673, filed on Apr. 18, 2002, now Pat. No. 6,738,438.

(51) Int. Cl.
*A61C 5/02* (2006.01)
*B21F 43/00* (2006.01)

(52) U.S. Cl. .......... 29/896.11; 29/896.1; 148/563; 148/670; 148/676; 433/102

(58) Field of Classification Search .......... 29/896.11, 29/896.1; 148/563, 675, 676, 669, 670; 433/102
See application file for complete search history.

(56) References Cited

U.S. PATENT DOCUMENTS

| | | | |
|---|---|---|---|
| 3,174,851 A | 3/1965 | Buehler et al. | 75/170 |
| 3,351,463 A | 11/1967 | Rozner et al. | 75/170 |
| 4,888,863 A | 12/1989 | Cox et al. | 29/156.8 B |
| 5,044,947 A | 9/1991 | Sachdeva et al. | 433/20 |
| 5,429,501 A | 7/1995 | Farzin-Nia et al. | 433/21 |
| 5,655,950 A | 8/1997 | Heath et al. | 451/48 |
| 5,762,541 A | 6/1998 | Heath et al. | 451/48 |
| 5,857,852 A | 1/1999 | Garman | 433/102 |

(Continued)

FOREIGN PATENT DOCUMENTS

EP 0 287 267 10/1988

(Continued)

OTHER PUBLICATIONS

Hodgson et al., *Shape Memory Alloys*, ASM Handbook, vol. 2, Properties and Selection: Nonferrous Alloys and Special-Purpose Materials, pp. 897-902, 1992.

(Continued)

*Primary Examiner*—David P Bryant
*Assistant Examiner*—Sarang Afzali
(74) *Attorney, Agent, or Firm*—Wood, Herron & Evans, LLP

(57) ABSTRACT

Method for manufacturing a dental instrument having a desired machined configuration, without twisting the instrument. A blank of superelastic material is brought to an annealed state comprising a phase structure including a rhombohedral phase alone or in combination with austenite and/or martensite, or a combination of martensite and austenite. In this annealed state, a portion of the annealed material is removed at low temperature, for example less than about 100° C., and advantageously at ambient temperature, to form a final machined configuration for the instrument. The instrument is then heat treated and rapidly quenched to a superelastic condition.

39 Claims, 4 Drawing Sheets

U.S. PATENT DOCUMENTS

| | | | |
|---|---|---|---|
| 5,882,198 A | 3/1999 | Taylor et al. | 433/102 |
| 5,941,760 A | 8/1999 | Heath et al. | 451/48 |
| 5,964,770 A | 10/1999 | Flomenblit et al. | 606/78 |
| 5,984,679 A | 11/1999 | Farzin-Nia et al. | 433/102 |
| 6,036,708 A | 3/2000 | Sciver | 606/159 |
| 6,131,579 A | 10/2000 | Thorson et al. | 128/898 |
| 6,149,501 A | 11/2000 | Farzin-Nia et al. | 451/48 |
| 6,158,304 A | 12/2000 | Packer et al. | 76/104 |
| 6,165,210 A | 12/2000 | Lau et al. | 623/1.12 |
| 6,293,020 B1 | 9/2001 | Julien | 30/350 |
| 6,299,445 B1 | 10/2001 | Garman | 433/102 |
| 6,315,558 B1 | 11/2001 | Farzin-Nia et al. | 433/102 |
| 6,428,634 B1 | 8/2002 | Besselink et al. | 148/421 |
| 6,569,194 B1 * | 5/2003 | Pelton | 623/1.15 |
| 6,783,438 B2 | 8/2004 | Aloise et al. | 451/48 |
| 7,338,441 B2 * | 3/2008 | Houser et al. | 600/206 |
| 2002/0137008 A1 * | 9/2002 | McSpadden et al. | 433/102 |
| 2003/0120181 A1 * | 6/2003 | Toma et al. | 600/585 |

FOREIGN PATENT DOCUMENTS

| | | |
|---|---|---|
| EP | 1354566 A2 | 10/2003 |
| WO | WO 99 37235 | 7/1999 |

OTHER PUBLICATIONS

Tobushi et al., *Recovery Stress Due to R-Phase Transformation in Ni-Ti Shape Memory Alloy*, Proceedings of First Int'l Conf. on Shape Memory and Superelastic Technologies, Asilomar Conference Ctrl, Pacific Grove, CA, USA, pp. 163-168, 1994.

European Patent Office, European Search Report and Examiner's Preliminary Opinion for EP Application No. 06254537.1, Nov. 20, 2006, 5 pp.

* cited by examiner

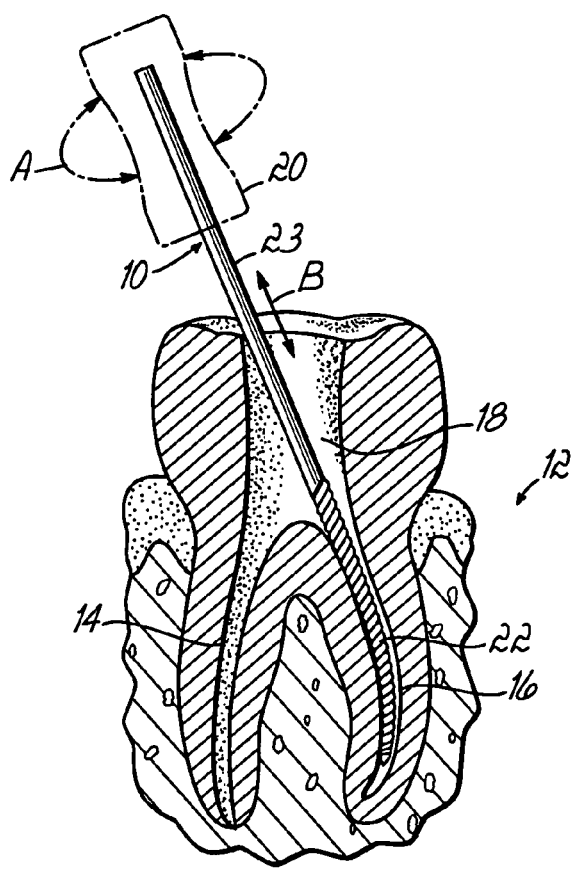
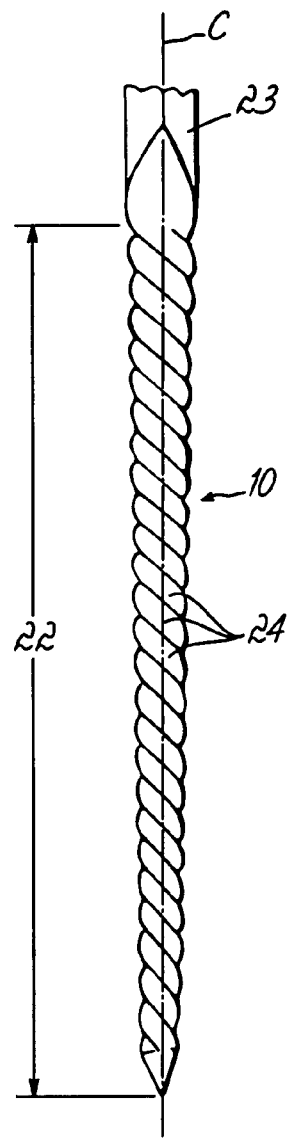
FIG. 1
FIG. 2A

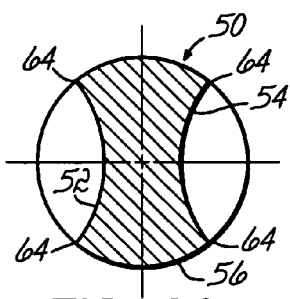
FIG. 4A
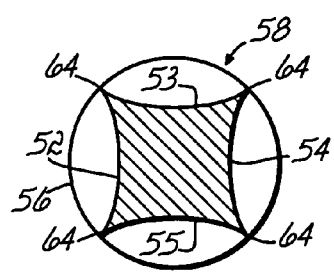
FIG. 4B
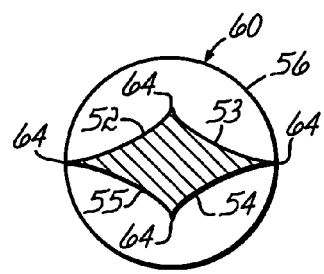
FIG. 4C
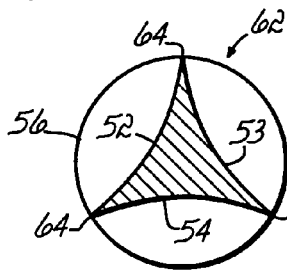
FIG. 4D
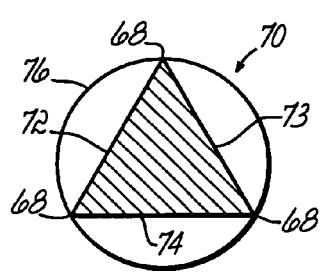
FIG. 4E
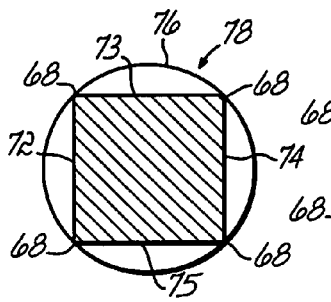
FIG. 4F
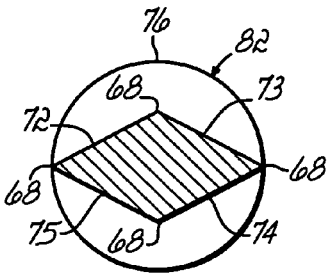
FIG. 4G
FIG. 4H
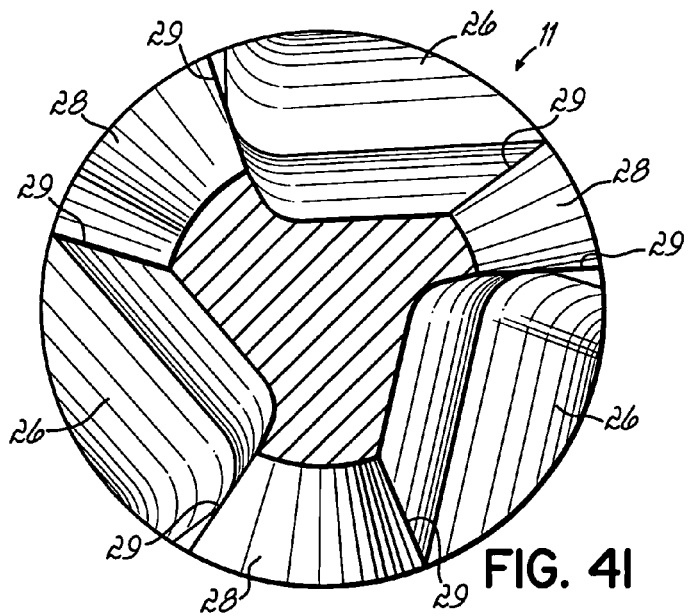
FIG. 4I

METHOD OF MANUFACTURING A DENTAL INSTRUMENT

CROSS-REFERENCE TO RELATED APPLICATION

This application is a continuation-in-part of commonly-owned U.S. patent application Ser. No. 10/797,552 filed Mar. 10, 2004 now U.S. Pat. No. 7,207,111 entitled METHOD OF MANUFACTURING AN ENDODONTIC INSTRUMENT, which is a divisional Ser. No. 10/125,673 filed on Apr. 18, 2002 of commonly-owned U.S. Pat. No. 6,783,438, the disclosures of which are incorporated by reference herein in their entirety.

FIELD OF THE INVENTION

The present invention generally relates to a method of machining dental instruments, such as endodontic files and reamers, and more specifically, to machining superelastic instruments.

BACKGROUND OF THE INVENTION

Endodontists use various types of instruments for cleaning and enlarging the root canals of the teeth. In a typical root canal procedure, an endodontist first makes an opening in the surface of the tooth to provide access to the interior. The endodontist then utilizes small instruments, such as hand-held files and reamers, to clean and enlarge the narrow, tapered root canals. In a conventional procedure, the endodontist fills the prepared root canals with gutta percha, which is a rubber-like substance, and then seals the tooth with protective cement. The endodontists may sometimes apply a crown to the tooth as a final step.

Typically, the endodontist uses a series of delicate, flexible files to clean out and shape the root canals. Each file includes a proximal end, typically including a handle to be gripped between the fingers of the endodontist, and a distal end or tip. A working length with a tissue-removing configuration, such as helical or non-helical flutes and cutting edges, is located between the proximal and distal ends. The endodontist uses files of increasingly larger diameter to sequentially increase the diameter of the root canal and achieve the desired diameter and shape.

Endodontic instruments of the desired type having helical flutes are conventionally fabricated by permanently twisting (also called torsioning) a rod of triangular, square, or rhomboid-shaped cross section. The angles formed between the surfaces form the cutting edges, which spiral along the working length of the instrument. Another method for manufacturing instruments of the described type having either helical or non-helical flutes is by a machining process wherein an instrument blank is moved past a rotating grinding wheel. The instrument blank is thereafter indexed and again moved past the grinding wheel, and these steps are repeated as many times as are necessary to form the instrument blank into the desired cross section. The flute grinding process produces a directional surface finish along the cutting axis, which can have a tendency to propagate early material failure and introduce machining stresses into the material.

Over the past several years, endodontic instruments having helical flutes have been manufactured by simultaneously grinding and twisting thin carbon steel or stainless steel rods or wires. Specifically, steel wire blanks are first ground to the desired cross sectional shape, such as square, triangular or rhomboid, and to the appropriate size and taper. The ground blank is then gripped at one end and spring loaded jaws are brought into contact with the ground portion of the blank. As the blank is rotated from the gripped end, the jaws are moved axially away from that end. The jaws therefore twist the rotating blank and form helical flutes into the blank. The longitudinal, ground edges of the blank form helical cutting edges on the file. The axial jaw speed, twisting speed and spring force are controlled to obtain the desired helical configuration.

Carbon and stainless steel instruments are generally stiff, which may lead to errors during root canal therapy. With the emergence of superelastic materials, such as nickel-titanium alloys, endodontic instrument manufacturers are now able to form endodontic root canal files and reamers with much more flexibility. This greatly assists the endodontist during use of the file or reamer in a root canal procedure. The use of superelastic material, however, causes some significant manufacturing concerns due to the tendency of the material to return to its original shape after the release of an applied force. File or reamer blanks manufactured of superelastic materials generally react in this manner to the conventional twisting methods employed for manufacturing carbon and stainless steel files and reamers. Moreover, if superelastic blanks are over-stressed, such as by being twisted too much during the fluting procedure, the material is subject to failure. For reasons such as these, current manufacturers of endodontic instruments may resort to grinding the helical profile directly into the superelastic blanks while applying no twisting forces to the blanks. These direct grinding methods tend to introduce stress into the material.

In U.S. Pat. No. 6,149,501, a method is provided for manufacturing superelastic endodontic instruments in which a blank is provided and maintained in the austenite phase, preferably above the austenite finish temperature (Af), at least prior to a twisting operation and, preferably, prior to and during the twisting operation. During the twisting operation, the material is converted from the austenite phase to the martensite phase by the stress applied during the twisting operation. Thus, the superelastic material undergoes stress-induced martensite transformation from a 100% austenite phase. For this method, high temperature tooling is required because the twisting operation is performed at a temperature above the Af temperature. The tooling and file blank are preferably submerged in a heated liquid, such as an oil or salt solution at a temperature of 500° C. or above, to bring the material to a 100% austenite phase. The heated liquids, however, are generally corrosive to the tooling.

In U.S. Pat. No. 6,783,438, a method is provided for manufacturing superelastic endodontic instruments in which prior to twisting, the superelastic material is brought to an annealed state comprising a phase structure that is a rhombohedral phase, a combination of an austenite phase and a martensite phase, a combination of a rhombohedral phase and an austenite phase, a combination of a rhombohedral phase and a martensite phase, or a combination of a rhombohedral phase, an austenite phase and a martensite phase. While in this annealed state, the instrument is twisted to form the helical flutes. While eliminating the need for high temperature tooling, a twisting apparatus is still needed to produce the desired configuration for the instrument, and the flutes may only be helical by virtue of the twisting operation.

With the above background in mind, there is a need for a method of fabricating endodontic instruments, such as files and reamers, that avoids the disadvantages described above for grinding and/or twisting techniques, that provide an instrument having a desired tissue-removing configuration, such as either helical or non-helical flutes, and for instruments that are flexible and highly resistant to torsional breakage. It would further be desirable to provide a method of manufacturing a wide variety of superelastic endodontic instruments that does not require high temperature tooling.

In addition to tissue-removing endodontic instruments, other superelastic dental instruments also suffer from the disadvantages of known machining techniques, such as high induced stresses in the machined material. Due to the small and precise configurations necessary for instruments that are used in the oral environment, such as orthodontic instruments and implants, the machining of configurations for dental instruments is particularly challenging. There is thus a need for a method of manufacturing a variety of superelastic dental instruments that avoids the disadvantages described above for machining techniques.

SUMMARY OF THE INVENTION

The present invention provides a method for forming superelastic dental instruments in which a machined configuration is formed for the instrument by first annealing a blank of superelastic material, and then removing a portion of the annealed material, such as at ambient temperature. To this end, a blank of superelastic material, such as a nickel-titanium alloy wire, is provided in or brought to an annealed state comprising a phase structure that is a rhombohedral phase, a combination of an austenite phase and a martensite phase, a combination of a rhombohedral phase and an austenite phase, a combination of a rhombohedral phase and a martensite phase, or a combination of a rhombohedral phase, an austenite phase and a martensite phase. In this annealed state, annealed material is removed, at ambient temperature for example, to form a machined configuration for the instrument. In accordance with one embodiment of the present invention, the instrument is an endodontic instrument and the machined configuration is a tissue-removing configuration, such as helical or non-helical flutes, and the configuration is formed without twisting the working length of the instrument. After the annealed material is removed, the dental instrument is then heat treated, for example at a temperature of at least about 300° C., followed immediately by rapid quenching to a superelastic condition. To provide the superelastic material in the annealed state, the material may be annealed at a temperature in the range of about 250-700° C., for example about 350-550° C., then cooled to ambient temperature. After rapidly quenching the heat treated instrument, the method may further comprise a stress relieving heat treatment, for example heating at a temperature in the range of about 150-300° C. for a period of about 2-6 hours.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

FIG. 1 is a cross-sectional view of a tooth and an endodontic instrument in accordance with the invention shown in use within a root canal.

FIG. 2A is a side view of an endodontic instrument in accordance with the invention having helical flutes.

FIGS. 4A-4I are transverse cross-sectional views, perpendicular to the center longitudinal axis of the instrument, formed using the apparatus of FIG. 3.

DETAILED DESCRIPTION

Figure 2B:
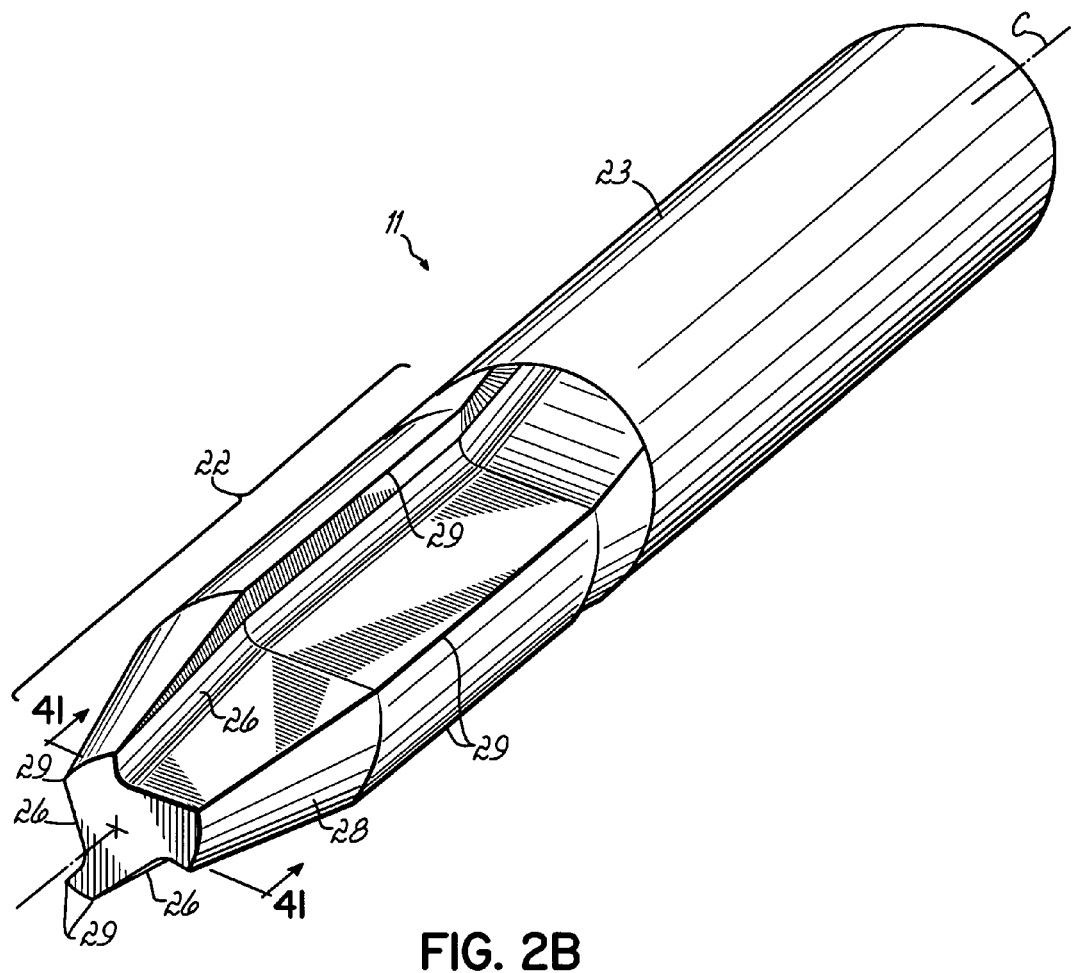
FIG. 2B is a perspective view of an endodontic instrument in accordance with the invention having non-helical flutes.

The present invention provides a method for manufacturing dental instruments. The method includes providing a blank of superelastic material in an annealed state, and then machining the annealed material to form the desired machined configuration for the instrument. The method of the present invention may be used for a variety of superelastic dental instruments used in the oral environment, which are by their nature small in size, often with very precise features, and thus difficult to manufacture. By virtue of the annealed state, in accordance with the present invention, the machining process is facilitated and stresses induced in the superelastic material are reduced or eliminated.

By way of example and not limitation, dental instruments may include endodontic instruments, orthodontic instruments, and implants. "Instrument" is used broadly herein to refer to any of a variety of devices that are used, temporarily or permanently, in the oral environment. Examples of endodontic instruments include files, reamers, pluggers, explorers, condensers, spreaders, ultrasonic tips, and microsurgical kits. Examples of orthodontic instruments include brackets, tiebacks, stops, arch wires, and appliances. Examples of implant instruments include fixtures, abutments, fixation components, screws, implant bodies, and prosthetic support structures. These examples of dental instruments are not meant to be exhaustive, and it may be appreciated that the method of the present invention may be used for any dental instrument formed from a superelastic material that may benefit from an improved machining process.

By "desired machined configuration" for the instrument, as used herein, is meant any desired form for the overall instrument that is created from the blank, whether it is a shape of a part of the instrument or a surface feature, including functional and non-functional surface features. For example, the method of the invention may be used to form the shape of the tie wings or the archwire slot in a bracket body or a surface pattern on the bonding base of the bracket. By further example, the method of the invention may be used to form the taper and/or the flutes on an endodontic file or reamer. Thus, material removal to form a machined configuration contemplates the formation of a variety of shapes and surface features.

For ease of illustration and discussion, the invention will now be described with reference to the making of endodontic instruments, in particular endodontic files, although the invention is more broadly applicable to a variety of dental instruments. Throughout the figures, like reference numerals are used to refer to like parts. Referring first to FIG. 1, an endodontic instrument 10 constructed in accordance with an embodiment of the present invention is shown being used during a root canal procedure on a tooth 12. Tooth 12 includes root canals 14, 16 and an upper interior portion 18 that has been initially opened using another instrument, such as a drill (not shown). Instrument 10 includes a handle 20 for manual gripping by, for example, an endodontist and a working length 22 having flutes, as will be discussed in more detail below. Although these instruments are typically manipulated manually, the invention may be adapted to power-operated instruments as well. In a conventional manner, instrument 10 may be rotated in the direction of arrows "A" and reciprocated in the direction of arrow "B" by the endodontist to clean out and enlarge root canal 16.

The working length 22 of the instrument 10 may include any desired tissue-removing configuration. For example, the configuration may include one or a combination of flutes, notches, discontinuous cutting edges, continuous cutting edges, sharp protrusions, abrading structure, or any other structure that removes tissue with a reciprocating and/or rotating motion of the instrument 10. By way of further example, the working length 22 of the instrument 10 may include helical flutes 24, as depicted in FIGS. 1 and 2A. Alternatively, an instrument 11 may be used in which the working length 22 comprises non-helical flutes 26, as depicted in FIG. 2B. Helical flutes 24 spiral around the center longitudinal axis C of the instrument 10, whereas non-helical flutes 26 extend along the center longitudinal axis C of the instrument 11 in axial alignment. For ease of discussion, the formation of helical or non-helical flutes will be described in detail below, though the invention is not so limited. Other tissue-removing configurations are contemplated.

Instruments of the present invention comprise a superelastic material. Superelastic materials are typically metal alloys that return to their original shape after substantial deformation. Superelastic alloys, such as nickel-titanium (NiTi) alloys, can withstand several times more strain than conventional materials, such as stainless steel, without becoming plastically deformed. Typically, superelastic alloys undergo a stress-induced martensitic transformation, which allows for shape memory properties. It may be appreciated by one skilled in the art that superelasticity is a function of composition and materials processing, and so a material is superelastic if its composition and processing history are such that it is capable of exhibiting superelastic properties. Shape memory and superelasticity may be found in stoichiometric NiTi, near-equiatomic Ni—Ti, for example 50.8 at. % Ti and 49.2 at. % Ni, Ni—Ti—Cu, Ni—Ti—Nb and Ni—Ti—Fe alloys as well as beta-phase titanium or other Ti based alloys. In an exemplary embodiment, superelastic materials for use in the present invention comprise at least about 40 at. % titanium. By way of further example, the superelastic material may be nickel-titanium or a nickel-titanium alloy further comprising niobium, copper, iron, chromium, cobalt, vanadium, hafnium or palladium. While not intending to be bound, exemplary NiTi alloys used in the present invention comprise about 52-57 at. % Ni for providing optimal shape memory and superelastic properties. For example, an exemplary alloy comprises 54-55 at. % Ni, balance Ti or balance Ti and one or more other alloy elements. Further exemplary alloys include 54Ni-46Ti and 41Ni-50Ti-9Nb.

The specific alloy composition used for the endodontic instrument of this invention is not critical, as the invention may utilize many materials that exhibit superelastic characteristics. For example, U.S. Pat. Nos. 5,044,947 and 5,429,501 disclose nickel-titanium-copper alloys and beta-phase titanium alloys, respectively, and U.S. Pat. No. 6,428,634 discloses NiTiNb alloys, any of which may be used in the present invention.

The present invention provides a method for forming superelastic endodontic instruments, such as files and reamers, wherein a material removing operation may be performed at low or ambient temperature, thereby eliminating the need for high temperature resistant tooling and corrosive high temperature salt baths, such that a safer process is provided. The low temperature may be, for example, less than about 100° C. In an exemplary embodiment, the material removal operation is performed at ambient temperature.

The first part of the method of the present invention involves providing a superelastic material, or a blank of superelastic material, in an annealed state comprising a phase structure including a rhombohedral phase, a combination of the rhombohedral phase with either or both of martensite and austenite, or a combination of the austenite phase and martensite phase. The term "blank" is used in a generic sense to refer to any form of the material, including by way of example and not limitation, material in the form of wire, rod or bar. The cross-sectional shape of the blank is not critical, for example, it may be circular or polygonal. The shape of the blank will depend on the type of dental instrument being formed. In an exemplary embodiment for making an endodontic instrument, an alloy that has been extruded into wire form may be used in the method of the present invention.

The superelastic material is provided in an annealed state to facilitate material removal and to reduce the stress induced in the remaining blank material during the removal process. The annealing treatment involves annealing the alloy at a temperature and for a time sufficient to bring the alloy to a state having a desired phase structure between 100% austenite and 100% martensite. In one embodiment, the phase structure includes a rhombohedral phase, which may also be referred to as an R-phase. As should be understood by those skilled in the art, phase structure refers to the internal crystal structure of a material, as opposed to an external physical shape. The rhombohedral phase may be the only phase, or the phase structure may further include austenite and/or martensite. Alternatively, the phase structure may be a combination of austenite and martensite. As may be understood by one skilled in the art, annealing refers to the heating of an alloy to a temperature and maintaining that temperature for a time sufficient to bring about a desired change in the alloy. The temperature sufficient for inducing the desired phase structure is dependent upon the particular alloy, but is generally in the range of about 250-700° C. for currently known superelastic materials, and by further example, in the range of about 350-550° C. The time sufficient for inducing the desired phase structure is also dependent upon the particular alloy and the size of the blank, as may be appreciated by one skilled in the art. Generally, the annealing time ranges from about 15 seconds to about 20 minutes, for example about 30 seconds to about 2 minutes. By way of further example only, and not limitation, a 1 mm diameter NiTi wire may be annealed at a temperature of about 495° C. for a period of 15 seconds to induce a phase comprising $90\% \leq$ austenite $< 100\%$, the remainder rhombohedral phase. Following annealing, the material is cooled to room or ambient temperature, upon which it remains in the annealed state comprising the desired phase structure. Thus, by this annealing method, there is provided an instrument blank or wire in an annealed state comprising a superelastic material in a rhombohedral phase alone or in combination with austenite and/or martensite, or in a phase structure that is a combination of austenite and martensite.

In one embodiment of the present invention, the superelastic material, for example a NiTi alloy, in ingot form, has an austenitic transformation temperature Af between about −11° C. and about −11° C. Superelastic alloys, when in the martensitic state (i.e., below Af, the temperature at which the material is about 100% austenite), retain their deformed shape when subjected to stress. However, the shape memory property returns the deformed material to its original pre-deformation configuration when heated above Af. In the present invention, providing an Af temperature well below body temperature (about 37° C.) will ensure that the dental instrument will be in the austenitic phase during use in the oral cavity. By "ingot form" is meant the as-cast ingot, prior to any forming of the ingot into a blank, for example, prior to drawing into wire form, and prior to providing the material in the annealed state.

It may be understood that the present invention contemplates that the manufacturer of the dental instrument may obtain a blank of superelastic material in the annealed state, whereby the manufacturer of the blank performs the annealing treatment, and the dental instrument manufacturer removes a portion of the annealed material to form the instrument having the desired configuration. Alternatively, the dental instrument manufacturer may obtain the blank of material in a non-annealed state, and perform the annealing treatment as part of the instrument manufacturing process.

In the second part of the method of the present invention, and again referring to endodontic instruments for ease of discussion, while the blank of material is in the annealed state, the final tissue-removing configuration (e.g., fluted configuration) for the instrument is formed by removing a portion of the annealed material generally from the surface of the blank to create a tissue-removing configuration (e.g., flute configuration, which may be either helical or non-helical). By virtue of the annealing treatment, the properties of the material are altered, which facilitates machining, and results in a decrease in the amount of induced stress to the material of the instrument from the machining process. Thus, the need for twisting or torsioning the working length of the instrument is eliminated, as is the need to pre-form the blank into a particular cross-section.

As used herein, material removal contemplates any known or hereafter-developed machining processes designed to remove unwanted material from a workpiece. Machining is a broad term that contemplates conventional machining operations, abrasive processes, and non-traditional machining processes. By way of example, conventional machining operations include turning, milling, shaping, etc. where material is removed from the workpiece generally in the form of chips. Abrasive processes include grinding, honing, lapping, etc. where small particles are removed by abrasion with a hard tool. Non-traditional machining processes include, for example, EDM (electrical discharge machining), WEDM (wire electrical discharge machining), ECM (electrical chemical machining), ECG (electrical chemical grinding), MDP (molecular decomposition process), ultrasonic machining, and chemical milling, where material is removed by physical mechanisms often on an atomic scale with little to no mechanical contact.

In EDM/WEDM, electric current flows through an electrolyte between a positively charged electrode and a negatively charged work piece (the instrument), although in some instances the charges can be reversed. In WEDM, the process uses a wire as the electrode in a pre-programmed path (CNC). The EDM/WEDM process involves disintegration of the work piece, and the fully controllable process is repeated with no heat, burr or distortion in the work piece. The process is capable of disintegrating metal as long as the metal is electrically conductive. Typically, a recast layer is re-deposited on the work piece, resulting in a harder surface, but this recast layer does typically possess a heat-affected zone.

In MDP, electric current flowing through the electrolyte between the positively charged work piece and the negatively charged abrasive wheel oxidizes the surface first, causing the material to soften. The soft surface is then "wiped away" by the abrasives in the wheel, and the fully controllable process is repeated with no heat, burr or distortion in the work piece. The MDP grinder has full capability to grind any metal as long as the metal conducts electrically.

In ECM, an anode (work piece) and a cathode (electrode) are electrically charged and positioned on a machine assembly (frame with one or more axes). An electrolyte is flushed through the adjusted gap between the work piece and the electrode. The electrolyte has the same function of conducting the current and carrying off the reaction products (metal ions, metal hydroxides, metal oxides, heat and gas) during the process that EDM or MDP have. By conducting an electrical current through the anode, electrolyte and cathode, anodic material will be dissolved locally until the product reaches the desired shape in any electrically conductive metal. ECG is the same as ECM, except that the cathode is shaped like a grinding wheel, but without using abrasives. No physical contact is made between the cathode and anode.

Thus, the material removal process that is performed after the material is annealed may be any known or hereafter-developed machining process suitable for forming the desired tissue-removing configuration, such as flutes with cutting edges. More specifically, the material removal process may be a conventional machining process, an abrasive process, or an unconventional machining process.

In one embodiment of the present invention, the material removal process includes turning and milling on swiss-turning equipment (also called a swiss-type lathe), such as that provided by Tornos SA, Marubeni Citizen or Star. In another embodiment, the material removal process removes a portion of the material from the blank in a spiral fashion around the center longitudinal axis of the working length so as to form one or more helical flutes along the working length of the instrument. In yet another embodiment, the material removal process removes a portion of material from the blank along one or more paths that are axially aligned with the center longitudinal axis of the working length so as to form one or more non-helical flutes along the working length of the instrument.

After the annealed blank is machined to form the final tissue-removing configuration, the instrument is heat treated, followed by rapidly quenching the instrument to a superelastic condition. The heat treatment may be at a temperature in the range of about 300-800° C., for example in the range of about 400-600° C. The heat treatment may be by a conventional heat-treat oven, electrical heating, inductance heating or by submerging the instrument in a heated liquid. The rapid quenching immediately follows the heat treatment whereby the instrument is cooled within a fraction of a second to a few seconds to a superelastic condition.

The instrument may be further subjected to a stress relieving heat treatment after quenching. To relieve stress within the material, the instrument may be heated, for example, to a temperature of about 150-300° C., such as by a conventional heat-treat oven, electrical heating, inductance heating or by submerging in a heated liquid. The stress relieving heat treatment may be performed, for example, for about 2-6 hours.

By the method of the present invention, there is thus provided a superelastic endodontic instrument, such as a file or reamer, having higher torsional and bending flexibility compared to conventional steel instruments, and manufactured by improved processes relative to prior superelastic instrument production techniques. Generally, the invention provides a process in which a superelastic endodontic instrument may be formed by annealing and machining at ambient or low temperature to produce a tissue removal instrument having superelastic properties. More generally, an improved method for machining a variety of dental instruments is provided, wherein the annealing facilitates the machining of the desired configuration and results in reduced stress in the superelastic material.

Figure 3:
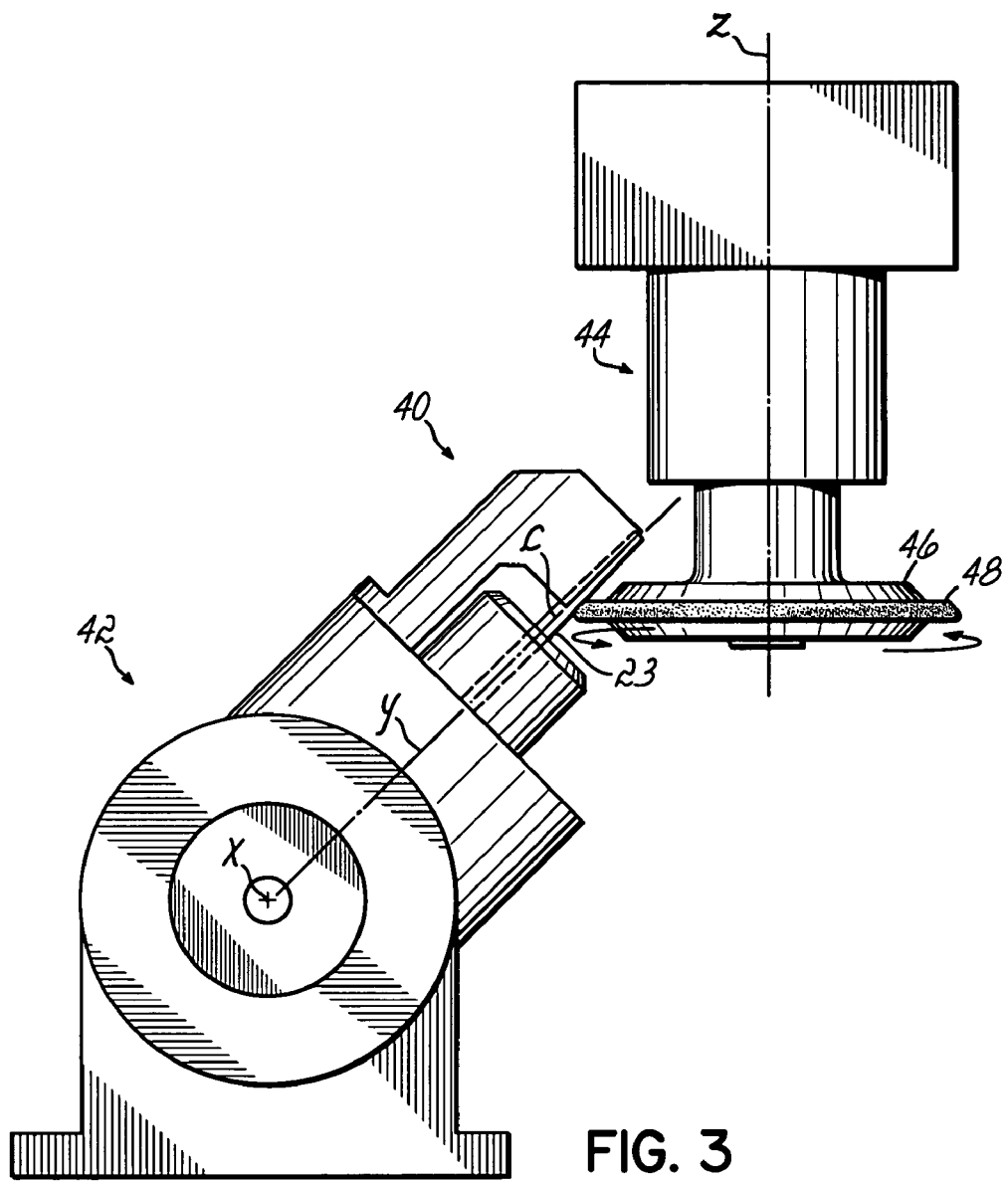
FIG. 3 is a schematic side view of an exemplary apparatus for forming endodontic instruments in accordance with the present invention.

When an EDM/WEDM technique is used in the method of the present invention for removing the annealed material to form the flutes (or other tissue-removing configuration) of the final instrument configuration, it may be implemented with an apparatus such as apparatus 40 depicted in FIG. 3. Apparatus 40 includes a "V" block support 42 with a simultaneous tilting axis X at 30-46° movement and a rotating axis Y at 360° movement. The "V" block support 42 is shown rotated 90° for clarity. Apparatus 40 further includes a machine spindle 44 rotatable about the center axis Z and having an electrode holder 46 for supporting a circular electrode 48. It may be appreciated by one skilled in the art that the electrode is a cathode in EDM/WEDM methods. The annealed blank 23 is held in the "V" block support 42 and adapted to be rotated about the central longitudinal axis C by rotating the "V" block support 42 about rotating axis Y. The movement of the annealed blank 23 and the electrode 48 may be in accordance with a pre-programmed path, digitally controlled by a CNC controller (not shown), to generate a flute pattern in accordance with a pattern programmed into the controller.

To form an endodontic instrument 10 having helical flutes 24, such as instrument 10 in FIG. 2A, the annealed blank 23 is held in the "V" block support 42 which is an indexing fixture, and the blank 23 is rotated about its center longitudinal axis C. While rotating, the annealed blank 23 is advanced past electrode 48 while the electrode is either held stationary or rotated about center axis Z. The annealed blank 23 is advanced past the electrode 48 at a relatively slow feed rate, for example about 0.25 to about 4 inches/minute so that the electrode 48 removes at least about 25% of the diameter of the annealed blank 23 at the point of maximum metal removal, and the material removal forms a helical surface or flute 24 on the working length 22 of the annealed blank 23. The annealed blank 23 is then rotatably indexed about its center longitudinal axis C not more than 180° by rotating "V" block support 42, and the annealed blank 23 is again advanced past the electrode 48 to form a second helical surface or flute 24 on the annealed blank 23. The indexing and flute forming steps may be repeated as many times as are necessary to form the desired number of helical flutes 24 on the working length 22 of the endodontic instrument 10.

To form an endodontic instrument 11 having non-helical flutes 26, such as instrument 11 in FIG. 2B, the annealed blank 23 is held stationary by "V" block support 42 and the electrode 48 is advanced at a relatively slow feed rate past the stationary annealed blank 23, for example so that the electrode removes at least about 25% of the diameter of the annealed blank 23 at the point of maximum metal removal, and the material removal forms a non-helical surface or flute 26 on the working length 22 of the annealed blank 23. By non-helical, it is meant that the flutes are aligned axially. The instrument blank 23 is then rotatably indexed about its center longitudinal axis C not more than 180° by rotating "V" block support 42, and the electrode 48 is again advanced past the annealed blank 23 to form a second non-helical flute 26. The indexing and flute forming steps are repeated as many times as are necessary to form the desired number of non-helical flutes 26 on the working length 22 of the endodontic instrument 11.

EDM, WEDM, MDP, ECG and ECM processes may offer a distinct advantage over traditional grinding techniques in manufacturing endodontic instruments. These processes disintegrate or remove material without direct contact of the electrode to the instrument blank, or by contact to a softened material, thereby reducing or eliminating any machining stresses induced by traditional grinding methods. The EDM and WEDM processes may also re-deposit material on the surface as the removed material is being disintegrated and cooled, which may result in a recast layer on the flute that has a surface hardness increase of at least about 15%, for example 15-25%, compared to the starting material of the blank, thereby providing a significantly harder and more resilient cutting edge. Moreover, the EDM, WEDM, MDP, ECG and ECM processes produce a non-directional surface finish, therefore eliminating inducement of early material failure propagated by directional surface finishes that result from grinding techniques. In addition, the blank is not required to be pre-ground to the desired cross-sectional shape prior to forming the flutes, as must be done in permanently twisting files to achieve desired helical flutes.

Another advantage of EDM, WEDM, MDP, ECG and ECM processes, with respect to endodontic instruments as well as other dental instruments, is that by adjusting the different variables associated with EDM, WEDM, MDP, ECG and ECM, the surface finish of the tissue-removing configuration of the instrument can be varied from fine to course, resulting in different abrading or cutting performances as well as variable surface hardness along cutting edges. Further, by producing different surface patterns or textures on the electrode and the ability of EDM, WEDM, MDP, ECG and ECM to transfer the reverse image on the surface of the electrode directly to the blank being processed, different surface textures and patterns may be produced on the surface of the instrument being machined by EDM, WEDM, MDP, ECG and ECM. Surface texturing and variable surface finishes enhance abrading and cutting performance for endodontic instruments, for example, or bonding performance for patterned orthodontic bracket bases. EDM, WEDM, MDP, ECG and ECM processes further increase the instrument elasticity. EDM, WEDM, MDP, ECG and ECM processes thus offer distinct advantages to the manufacture of dental instruments that have not heretofore been recognized.

The EDM, WEDM, MDP, ECG and ECM processes further provide high flexibility with respect to the particular design of the flutes that may be achieved for the endodontic instruments. FIGS. 4A-4I provide transverse cross-sectional views of various exemplary flute designs that may be formed in accordance with the invention. FIG. 4A provides a cross section of an instrument 50 having two continuous helical flutes 52, 54 formed in the peripheral surface of annealed blank 56. In the method of the present invention, the first flute 52 is formed by EDM or ECM, and then the annealed blank 56 is indexed 180° and the second flute 54 is formed by EDM or ECM.

Two additional flutes 53, 55 may be formed to provide instrument 58 as shown in cross section in FIG. 4B. The method to produce instrument 58 may include forming flute 52 by EDM or ECM, then indexing the blank 56 by 90°; forming the second flute 53, then indexing the blank 56 by 90°; forming the third flute 54, then indexing the blank 56 by 90°; and finally forming the fourth flute 55. Alternatively, the method may include forming the first flute 52, then indexing the blank 56 by 180°; forming the second flute 54, then indexing the blank by 90°; forming the third flute 53, then indexing the blank 56 by 180°; and forming the fourth flute 55.

Instrument 60 shown in cross section in FIG. 4C is similar to instrument 58 in that it has four flutes 52, 53, 54, 55, but instead has a rhomboidal transverse cross section. The method for forming instrument 60 includes forming the first flute 52, then indexing the blank 56 by 120°; forming the second flute 53, then indexing the blank 56 by 60°; forming the third flute 54, then indexing the blank 56 by 120°; and finally forming the fourth flute 55.

Instrument 62 depicted in cross section in FIG. 4D has three flutes 52, 53, 54 and a triangular transverse cross section. Instrument 62 may be manufactured by indexing the file blank 56 by 120° increments. In each of FIGS. 4A-4D, the machined surfaces or flutes 52, 53, 54, 55 have a concave shape. The apices between the concave surfaces form the helical cutting edges 64, which in each of the Figures, include either three or four cutting edges 64. Due to the concave shape of the flutes, the angle of the apices is more acute, which provides a sharp cutting edge 64.

FIGS. 4E-4G depict various transverse cross sections for instruments having flat flutes, as opposed to the concave flutes in FIGS. 4A-4D. The apices between the flat surfaces form the helical cutting edges 68, which in each of the Figures, include either three or four cutting edges 68. Due to the flat shape of the flutes, the angle of the apices is less acute, which provides a more rugged cutting edge 68 that will exhibit a longer working life. The acute cutting edges in FIGS. 4A-4D are sharp but weaker due to the lower amount of material, and the less acute cutting edges in FIGS. 4E-4H are less sharp but more rugged with a longer working life.

Instrument 70 depicted in cross section in FIG. 4E has a triangular transverse cross section formed by three flat helical flutes 72, 73, 74, which may be formed by ECM or EDM sequentially with 120° indexing of the annealed blank 76 between forming steps. Instrument 78 depicted in FIG. 4F has a square transverse cross section, for example taken along line 4F of FIG. 2A, and has four flat helical flutes 72, 73, 74, 75. Instrument 78 may be formed by the same method used to form instrument 58 of FIG. 4B, but using a cutting path that forms flat surfaces rather than concave surfaces.

Instrument 80 depicted in FIG. 4G also has four flat helical flutes 72, 73, 74, 75, but has a rectangular transverse cross section. With respect to the method for forming instrument 80, for example, the first flat surface or flute 72 may be formed by EDM or ECM, then the instrument blank 76 is indexed by 90°. The initial depth of cut is increased and the second flat surface or flute 73 is formed by EDM or ECM. Instrument blank 76 is again indexed 90° and the initial depth of cut is reduced to form flute 74. Then, the blank 76 is indexed a final 90° and the initial depth of cut increased to form flute 75. Alternatively, flute 72 may be formed by EDM or ECM, then the instrument blank is indexed by 180° and the flute 74 is formed. The blank 76 is then indexed by 90° and the initial depth of cut increased and flute 73 is formed. Then, the blank 76 is indexed 180° and flute 75 is formed.

Instrument 82 depicted in FIG. 4H also has flat helical flutes 72, 73, 74 and 75, but has a rhomboidal transverse cross section. The method for forming instrument 82 includes forming flute 72, then indexing the blank 76 by 120°; forming flute 73, then indexing the blank 76 by 60°; forming flute 74, then indexing the blank 76 by 120°; and finally forming flute 75. It is not necessary to change the initial depth of cut to fabricate the square, triangular and rhomboidal instruments.

FIG. 4I depicts the transverse cross section along line 4I of the instrument 11 of FIG. 1B having non-helical flutes 26 with concave surfaces. In this exemplary embodiment, the flutes 26 are non-uniformly concave, with convex lands 28 there between. Apices are formed where the flutes 26 meet the lands 28 to form six cutting edges 29. The flutes 26 and thus cutting edges 29 are tapered along the working length 22. The EDM and ECM processes used in accordance with the present invention allow for easy manufacture of endodontic instruments having complicated profiles such as that depicted in FIGS. 2B and 4I. It may be appreciated, however, that other profiles other than that shown may be formed in accordance with the present invention.

In addition to the above embodiments describing the use of EDM, WEDM, MDP, ECG and ECM for forming the flutes, other machining processes are also useful in forming the tissue-removing configuration along the working length from the annealed blank, and in forming other desired machined configurations in other dental instruments. By virtue of the annealed state, material removal is facilitated and less stress is induced in the instrument material. Thus, the present invention provides a dental instrument having a machined configuration, such as one or more helical or non-helical flutes in the working length of an endodontic instrument, prepared by first annealing a blank of superelastic material, and then machining the blank to form the final machined configuration along the working length of the instrument, with the proviso that the working length is not subjected to a twisting operation.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope of the general inventive concept.

What is claimed is:

1. A method for forming a machined configuration in a surface of a superelastic dental instrument, comprising:
   providing a blank of superelastic material in an annealed state comprising a phase structure selected from a rhombohedral phase, a combination of an austenite phase and a martensite phase, a combination of a rhombohedral phase and an austenite phase, a combination of a rhombohedral phase and a martensite phase, and a combination of a rhombohedral phase, an austenite phase and a martensite phase;
   while in the annealed state, removing a portion of the superelastic material from the blank to form a machined configuration for the instrument; and
   thereafter, heat treating the instrument, followed by rapidly quenching the instrument to a superelastic condition.

2. The method of claim 1 wherein the instrument is an endodontic instrument, and the machined configuration formed for the instrument is a tissue-removing configuration along the working length of the endodontic instrument.

3. The method of claim 2 with the proviso that the working length is not twisted to form a final tissue-removing configuration.

4. The method of claim 2 wherein the material is removed in spiral fashion around a center longitudinal axis of the working length to form the tissue-removing configuration as one or more helical flutes.

5. The method of claim 2 wherein the material is removed along one or more paths axially aligned with a center longitudinal axis of the working length to form the tissue-removing configuration as one or more non-helical flutes.

6. The method of claim 1 wherein the superelastic material comprises at least about 40 at. % titanium.

7. The method of claim 6 wherein the superelastic material is a nickel-titanium alloy.

8. The method of claim 7 wherein the nickel-titanium alloy further comprises an element selected from niobium, copper, iron, chromium, cobalt, vanadium, hafnium and palladium.

9. The method of claim 1 wherein removing the material is by a method selected from electrical discharge machining, wire electrical discharge machining, electrical chemical grinding, electrical chemical machining, and molecular decomposition process.

10. The method of claim 1 wherein removing the material is by turning and milling using a Swiss-turning machine.

11. The method of claim 1 wherein the superelastic material, in an as-cast ingot form and prior to being provided in the annealed state, has an Af in the range of about −1° to about −11° C.

12. The method of claim 1 wherein heat treating the instrument is at a temperature in the range of about 400-600° C.

13. The method of claim 1 further comprising, after rapidly quenching, heating the instrument to a temperature in the range of about 150-300° C. to relieve stress therein.

14. The method of claim 1 wherein the instrument is provided in an annealed state comprising the rhombohedral phase.

15. The method of claim 1 wherein removing the material is by a method selected from electrical discharge machining and wire electrical discharge machining, including removing at least about 25% of a diameter of a starting material at a point of maximum metal removal, the starting material having a first hardness, and redepositing at least a portion of the removed material on the blank to form a recast layer having a second hardness of at least about 15% greater than the first hardness.

16. A method for forming one or more flutes along a working length of a superelastic endodontic instrument comprising:
    annealing a blank of superelastic material at a temperature in the range of about 250-700° C. to an annealed state comprising a phase structure selected from a rhombohedral phase, a combination of an austenite phase and a martensite phase, a combination of a rhombohedral phase and an austenite phase, a combination of a rhombohedral phase and a martensite phase, and a combination of a rhombohedral phase, an austenite phase and a martensite phase, and cooling the annealed material to ambient temperature;
    while in the annealed state, removing a portion of the annealed material from the blank at ambient temperature to form a final tissue-removing configuration along the working length of the instrument, with the proviso that the working length is not twisted to form the final tissue-removing configuration; and
    thereafter, heat treating the instrument at a temperature in the range of about 300-800° C., followed by rapidly quenching the instrument to a superelastic condition.

17. The method of claim 16 wherein the superelastic material comprises at least about 40 at. % titanium.

18. The method of claim 17 wherein the superelastic material is a nickel-titanium alloy.

19. The method of claim 18 wherein the nickel-titanium alloy further comprises an element selected from niobium, copper, iron, chromium, cobalt, vanadium, hafnium and palladium.

20. The method of claim 16 further comprising, after rapidly quenching, heating the instrument to a temperature in the range of about 150-300° C. to relieve stress therein.

21. The method of claim 20 wherein the instrument is heated for a period of about 2-6 hours.

22. The method of claim 16 wherein annealing the superelastic material is at a temperature in the range of about 350-550° C.

23. The method of claim 16 wherein annealing the superelastic material is at a temperature sufficient to provide a phase structure including the rhombohedral phase.

24. The method of claim 16 wherein heat treating the instrument is at a temperature in the range of about 400-600° C.

25. The method of claim 16 wherein the superelastic material, in an as-cast ingot form and prior to being provided in the annealed state, has an Af in the range of about −1° to about −11° C.

26. The method of claim 16 wherein the material is removed in spiral fashion around a center longitudinal axis of the working length to form the tissue-removing configuration as one or more helical flutes.

27. The method of claim 16 wherein the material is removed along one or more paths axially aligned with a center longitudinal axis of the working length to form the tissue-removing configuration as one or more non-helical flutes.

28. The method of claim 16 wherein removing the material is by a method selected from electrical discharge machining, wire electrical discharge machining, electrical chemical grinding, electrical chemical machining, and molecular decomposition process.

29. The method of claim 16 wherein removing the material is by turning and milling using a Swiss-turning machine.

30. The method of claim 16 wherein removing the material is by a method selected from electrical discharge machining and wire electrical discharge machining, including removing at least about 25% of a diameter of a starting material at a point of maximum metal removal, the starting material having a first hardness, and redepositing at least a portion of the removed material on the blank to form a recast layer having a second hardness of at least about 15% greater than the first hardness.

31. A method for forming a machined configuration in a surface of a superelastic dental instrument, comprising:
    annealing a blank of superelastic material to convert the superelastic material to an annealed non-superelastic state comprising an annealed material having a phase structure selected from a rhombohedral phase, a combination of an austenite phase and a martensite phase, a combination of a rhombohedral phase and an austenite phase, a combination of a rhombohedral phase and a martensite phase, and a combination of a rhombohedral phase, an austenite phase and a martensite phase;
    while in the annealed non-superelastic state, removing a portion of the annealed material from the blank to form a machined configuration for the instrument; and
    thereafter, heat treating the instrument, followed by rapidly quenching the instrument to return the annealed material to a superelastic state.

32. The method of claim 31 wherein the instrument is an endodontic instrument, and the machined configuration formed for the instrument is a tissue-removing configuration along the working length of the endodontic instrument.

33. The method of claim 32 with the proviso that the working length is not twisted to form a final tissue-removing configuration.

34. The method of claim 31 wherein the superelastic material is a nickel-titanium alloy.

35. The method of claim 31 wherein the superelastic material, in an as-cast ingot form and prior to being annealed to the annealed non-superelastic state, has an Af in the range of about −1° to about −11° C.

36. The method of claim 31 wherein heat treating the instrument is at a temperature in the range of about 400-600° C.

37. The method of claim 31 further comprising, after rapidly quenching, heating the instrument to a temperature in the range of about 150-300° C. to relieve stress therein.

38. The method of claim 31 wherein annealing the superelastic material is at a temperature in the range of about 350-550° C.

39. The method of claim 31 wherein annealing the superelastic material is at a temperature sufficient to provide a phase structure including the rhombohedral phase.

* * * * *

UNITED STATES PATENT AND TRADEMARK OFFICE
CERTIFICATE OF CORRECTION

PATENT NO. : 7,779,542 B2 Page 1 of 1
APPLICATION NO. : 11/216890
DATED : August 24, 2010
INVENTOR(S) : Aloise et al.

It is certified that error appears in the above-identified patent and that said Letters Patent is hereby corrected as shown below:

Col. 1, lines 11-12, "which is a divisional Ser. No. 10/125,673 filed on Apr. 18, 2002 of commonly-owned U.S. Pat. No. 6,783,438," should read --which is a divisional of commonly-owned Ser. No. 10/125,673 filed on Apr. 18, 2002, now U.S. Pat. No. 6,783,438,--.

Col. 6, line 54, "between about -11°" should read --between about -1°--.

Signed and Sealed this

Sixteenth Day of November, 2010

David J. Kappos
*Director of the United States Patent and Trademark Office*